United States Patent
Goldenberg

(10) Patent No.: US 7,338,456 B2
(45) Date of Patent: Mar. 4, 2008

(54) BONE MARROW BIOPSY NEEDLE

(76) Inventor: Alec S. Goldenberg, 157 E. 32nd St., Second Floor, New York, NY (US) 10016

( * ) Notice: Subject to any disclaimer, the term of this patent is extended or adjusted under 35 U.S.C. 154(b) by 0 days.

(21) Appl. No.: 11/416,451

(22) Filed: May 1, 2006

(65) Prior Publication Data

US 2007/0255171 A1 Nov. 1, 2007

(51) Int. Cl.
*A61B 10/00* (2006.01)
(52) U.S. Cl. .................................... 600/564
(58) Field of Classification Search ............ 600/564
See application file for complete search history.

(56) References Cited

U.S. PATENT DOCUMENTS 5,634,473 A * 6/1997 Goldenberg et al. ........ 600/567
6,471,709 B1 * 10/2002 Fawzi et al. ................ 606/114

* cited by examiner

*Primary Examiner*—Max Hindenburg
*Assistant Examiner*—Emily M Lloyd

(57) ABSTRACT

A biopsy needle for removal of tissue from a patient includes an outer tube having a distal end that has an inner diameter (IDtip) and an inner tube within the outer tube and having an inner diameter (IDsc), defined at the distalmost section of the inner tube. The needle also includes a snare having a first end connected to the inner tube and a second end coupled to the outer tube. The snare has a variable diameter that is controlled by rotation of the inner tube with respect to the outer tube in a prescribed direction resulting in the opening and closing, respectively, of the snare. A ratio (R) defined as (IDsc)/(IDtip) is greater than 1.

18 Claims, 4 Drawing Sheets

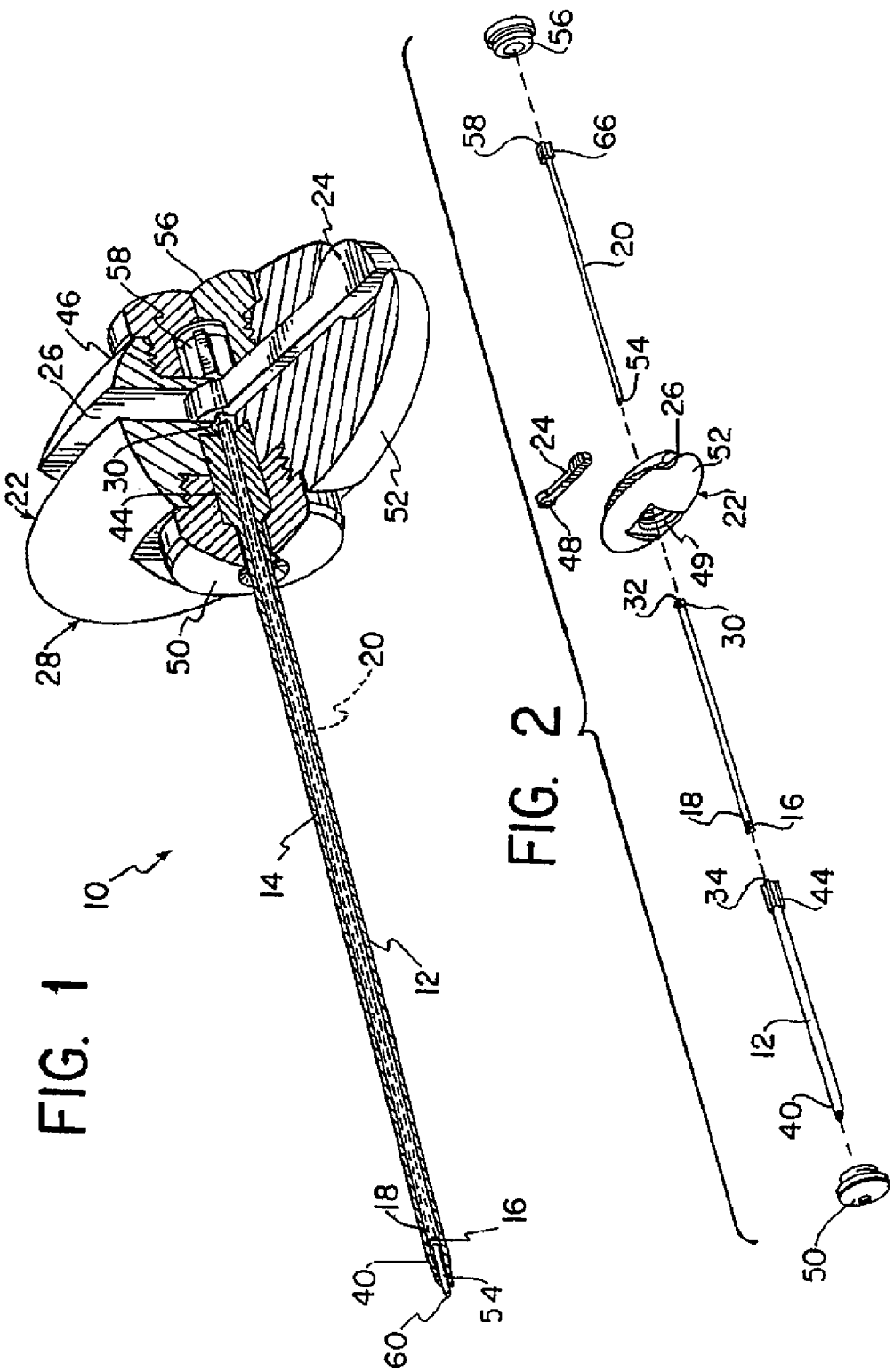

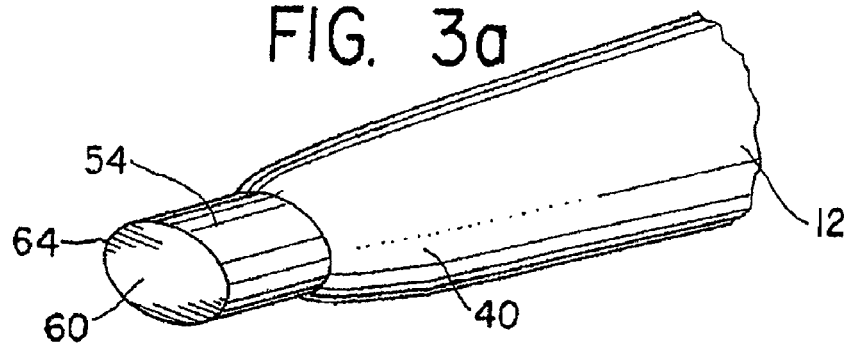
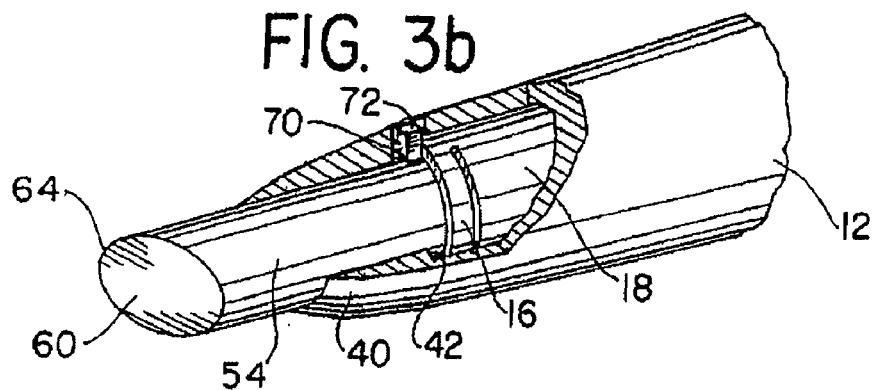
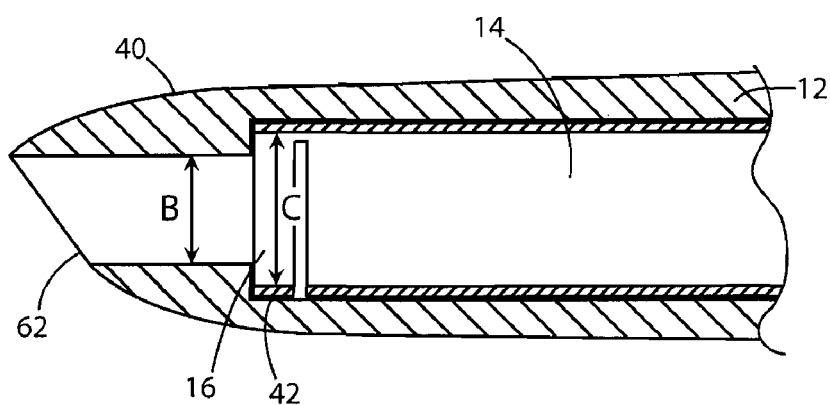

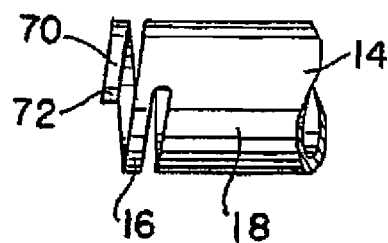
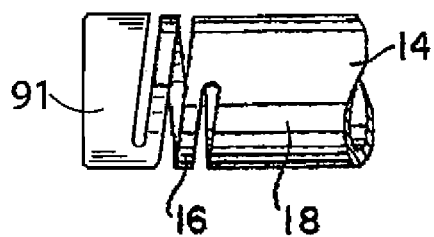
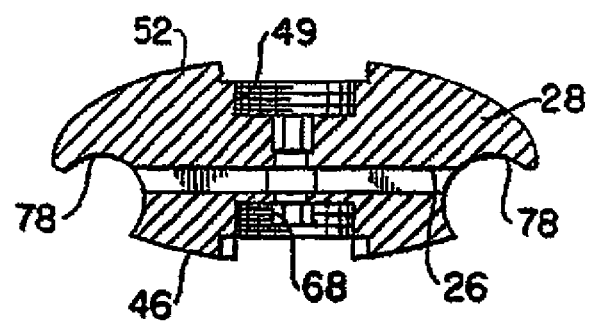

BONE MARROW BIOPSY NEEDLE

FIELD OF THE INVENTION

This invention relates generally to a surgical instrument, known variously as a biopsy needle or cannula that is used to gather tissue, such as bone marrow, from living persons or animals for pathological study. More specifically, the invention relates to a biopsy needle having an improved structure for severing a tissue sample and/or retaining the tissue sample within the needle.

BACKGROUND

For various medical reasons, such as evaluating the histology and/or pathology of a tissue, it is often necessary for a physician to obtain a sample of a patient's body tissue. In particular, bone marrow is frequently retrieved to study its cellularity and potential infiltration with abnormal cells. The currently available procedures and instruments used for obtaining bone marrow biopsy samples, while not overly complex, almost universally result in excessive patient discomfort and often recover inadequate quantities of biopsy material which sometimes is distorted and/or difficult to interpret. In the standard bone marrow procurement protocol, using currently available instruments, (such as those disclosed in U.S. Pat. No. 4,262,676 to Khosrow Jamshidi), the patient is prepared with a suitable local anesthetic at the posterior superior iliac crest/spine. Then, a relatively narrow needle is inserted to obtain an aspirate of liquid bone marrow material to make slides for examination of cellular morphology and to evaluate the surface immunophenotype of the bone marrow cells with flow cytometry. This portion of the procedure, referred to as the bone marrow aspiration, is generally relatively less painful than the bone marrow biopsy procedure using a conventional biopsy needle. Using newer bone marrow biopsy needles which actively capture specimens, and minimize manipulation of the needle after insertion, the aspirate procedure appears to be more painful than the biopsy procedure.

After the aspirate is obtained, if necessary, a biopsy of the bone marrow is taken. A significantly wider bore needle having an inner diameter that will accommodate a suitable marrow sample is prepared with an inner stylet that extends beyond the distal end of the outer needle. The stylet's distal end may be cut at an angle, with the leading edge sufficiently sharp to pierce tissue and bone. With the stylet in place within the outer needle, the needle is pushed through the outer layers of skin and subcutaneous tissue until the needle tip reaches the surface of the cortical bone. The needle and stylet are then pushed into and through the cortical layer until the tip has penetrated into the bone marrow space.

The stylet is then removed from the proximal end of the needle, which opens up the core of the needle to accommodate entry of bone marrow material for collection and retrieval. The needle is then usually advanced another 1 to 2 centimeters at minimum with a slight twisting motion. Often, the distal end of the needle will also be provided with an angled cut and sharpened leading edge to facilitate cutting and coring the tissue. By providing a slight twisting motion as the needle is advanced, usually with no more than quarter or half turns, an appropriate sample is cored from the marrow tissue and enters the inner passage of the marrow needle.

At this point, the marrow biopsy sample is ready to be removed from the patient, although it is important that the biopsy remain within the needle as the needle is withdrawn to ensure recovery of the specimen. If the biopsy becomes dislodged and falls through the distal end of the biopsy needle, the specimen is irretrievably lost. The procedure is then unsuccessful and must be repeated from the beginning.

Various methods have been utilized by physicians to try to prevent the biopsy specimen from dislodging from the needle. For example, after the needle has entered the bone and fully cored a sample from the marrow, some physicians will pull the biopsy needle back a few millimeters and then advance it a few millimeters at a different angle than the first insertion. This theoretically will "cut" the biopsy piece at the tip of the needle. Other physicians attempt to dislodge or disrupt the connection between the specimen and the bone by making multiple complete clockwise and counterclockwise rotations of the biopsy needle while within the bone. Some physicians even hit the proximal end of the biopsy needle at its handle in an attempt to mechanically disrupt the connection between the specimen and the additional bone.

As can be plainly realized, these manipulations at the end of the procedure, attempts at ensuring that the specimen remains within the needle, can often produce substantial discomfort and anxiety to the patient. Sometimes when the bone marrow is very soft, as in patients with osteoporosis, almost all of these attempts are futile because the bone structure is so fragile. Conversely, sometimes when the bone marrow is very fibrotic, which occurs in patients with myelofibrotic diseases or in AIDS patients, it is difficult to dislodge the core biopsy, since the bone marrow itself is reinforced by the surrounding tissue. In those cases, the cored biopsy often remains attached to the bone and is not successfully recovered.

Other attempts at designing a more efficient and successful biopsy needle have met with little or no success, for various reasons, including the complexity of the devices. For example, U.S. Pat. No. 3,605,721 to Hallac, discloses a biopsy needle in which an inner tube has a weakened portion represented by strips extending between distal and proximal portions of the inner tube. The distal portion of the inner tube is adhered to an outer tube and will not rotate. Once a biopsy has entered the needle, the proximal portion of the inner tube is rotated, causing the strips to twist together and eventually break off. This twisting motion tends to twist the strips to the tube's center, thus hopefully keeping the biopsy piece proximal of the twisted and broken strips for later removal. This particular biopsy needle is only a disposable device, since the strips are broken or irreversibly warped by deformation during the twisting process. Another disadvantage is the lack of control over the twisting motions or the breakage of the strips. Essentially, the operator is left to twist the inner tube until resistance to that twisting is lost, indicating that the strips have severed. There is also no way of releasing the device's grip on tissue during the procedure, should any problems arise.

U.S. Pat. No. 5,074,311 to Hasson discloses a biopsy device that includes a pair of inner jaws that can be actuated within the outer needle to "bite off" any biopsy piece that has entered the needle. The disadvantages of this device include multiple small mechanical linkages and parts including pivot pins, which are extremely difficult and expensive to assemble and maintain, in addition to the greatly increased chance of mechanical failure resulting in failure to retrieve an adequate specimen.

U.S. Pat. No. 5,522,398, to Goldenberg et al., discloses a bone marrow biopsy needle; however, the patent teaches that an inner diameter B at the distal tip of the needle (as shown in FIG. 4 thereof) is substantially equal to an inner diameter C of the inner tube (as shown in FIG. 3C) so that there will be no ridge or lip within the instrument to impede tissue entering the inner lumen of the needle. However, observations over time of the performance of needles constructed in this manner indicates that such a relationship may impede specimen transit into and through the needle, and that a virtual obstruction phenomena may develop as a result of the above relationship between the two inner diameters. Compromise of specimen transit into the needle results in an inability of the specimen to move forward into the lumen of the needle. In addition, as the needle penetrates tissue, external pressures, especially those produced by dense bone, could deform or change the diameter at the needle tip (inner diameter B) or might transmit a force through the wall of the needle, marginally decreasing the diameter of the inner tube or snare (inner diameter C). These changes could dynamically alter the relationship between the inner diameters and cause a virtual obstruction, impeding specimen transit and making it difficult for the specimen to move forward into the needle.

SUMMARY

In view of the deficiencies noted in the prior references and the current protocols, it is an object of the present invention to provide an improved biopsy needle that will sever a tissue sample from surrounding tissue or hold it with sufficient force such that the action of removing the needle detaches the piece from the surrounding tissue.

It is another object of the invention to provide a biopsy needle that requires minimal manipulation of the needle at the end of the procedure, thus decreasing patient pain and anxiety.

It is a further object of the invention to ensure obtaining a biopsy sample with each attempt, thus decreasing the number of necessary biopsy attempts, and the time, effort and money expended on the overall procedure.

It is yet another object of the invention to provide a biopsy needle that is simple and inexpensive to manufacture, may be reusable, and is simple to operate.

According to the objects of the invention, an improved biopsy needle has an outer cannula, an inner tube and a stylet. The distal end of the inner tube is provided with a snare in the form of a coil extending from the inner tube. The free end of the coil is adhered to the outer cannula. Upon rotation of the inner tube with respect to the outer cannula, the coil will decrease in diameter to either sever or hold the biopsy piece within the outer needle. After removal of the needle from the patient, rotating the inner tube in the opposite direction will cause the coil to expand to its original diameter and allow the biopsy piece to be removed from the needle.

In yet another aspect, a biopsy needle for removal of tissue from a patient, according to one embodiment, includes an outer tube having a distal end, contributing to a needle tip, that has an inner diameter ($ID_{tip}$) and an inner tube within said outer tube. The needle also includes a snare having a first proximal end connected to the inner tube and having an inner distal diameter ($ID_{sc}$) and a second distal end coupled to the outer tube. The snare has a variable diameter that is controlled by rotation of the inner tube with respect to the outer tube in a prescribed direction resulting in the opening and closing, respectively, of the snare, wherein a ratio $(R)=(ID_{sc})/(ID_{tip})$ is greater than 1.

BRIEF DESCRIPTION OF THE DRAWINGS

Other objects, advantages and embodiments than those described above will become apparent to those skilled in the art upon reading the following detailed description of the preferred embodiments in conjunction with a review of the appended drawings, in which:

FIG. 1 is a perspective view of a biopsy needle in accordance with the present invention;

FIG. 2 is an exploded view of the biopsy needle according to the present invention;

FIGS. 3a-3e are detail perspective views of the distal ends of various components during operation of the biopsy needle;

FIG. 6A is a detail side view of the inner tube of the present invention according to one embodiment;

FIG. 6B is a detail side view of the inner tube of the present invention according to another embodiment; and FIG. 7 is a cross-section view through the handle piece of the biopsy needle.

DETAILED DESCRIPTION OF THE PREFERRED EMBODIMENTS

Figure 3D:
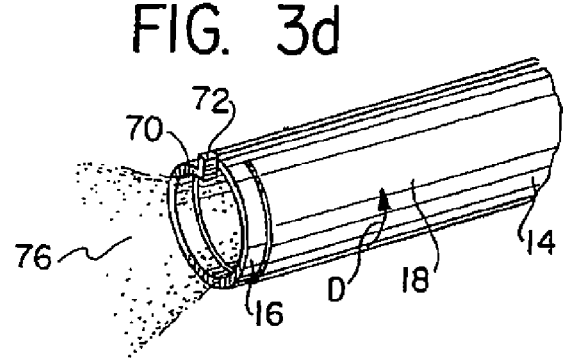

Referring now to FIGS. 1 and 2, a biopsy needle 10 has an outer cannula 12, an inner tube 14 with a snare 16 at its distal end 18, a stylet 20, and a handle assembly 22. In FIG. 2, the assembly of the present biopsy needle 10 is shown in an exploded view.

As part of the handle assembly 22, a lever 24 fits into a corresponding groove 26 within a handle piece 28. The lever 24 actuates the snare 16 within the outer cannula 12 without any movement of the outer cannula 12 relative to the patient (not shown). The functioning of this lever 24 is described more fully below. The inner tube 14 has a snare 16 at its distal end 18 and a gear or lever connector 30 mounted on its proximal end 32. The inner tube 14 is inserted into the proximal end 34 of the outer cannula 12 with the gear or lever connector 30 extending out of the proximal end 34, which facilitates connection of the lever to the inner tube and uniform conversion of lever rotation to inner tube rotation.

Figure 4:
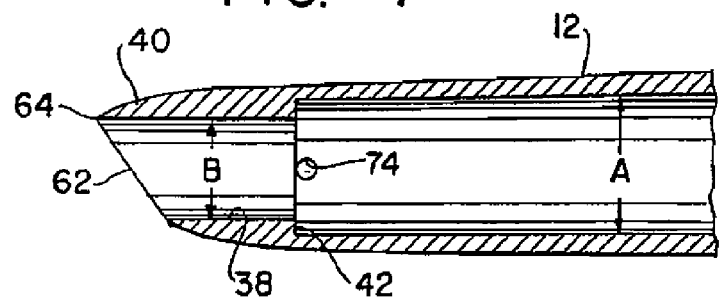
FIG. 4 is a cross-section of the distal end of the outer cannula.

As can be seen in FIG. 4, the interior of the outer cannula 12 has a constant inner diameter A along a majority of its length, and a portion 38 having a smaller inner diameter B at its distal tip 40 allowing the inner tube to fit within the outer tube while keeping the inner diameter of the inner tube C nearly equivalent to the inner diameter of the distal tip B.

In contrast to the teachings of the present inventor's prior '398 patent, the present applicant has discovered that the narrow inner diameter B at the distal tip 40 should not be substantially equal to the inner diameter C of the inner tube 14 in order to optimize the ability of the specimen to move forward into the needle. The ability of the specimen to move forward into the needle 10 can be described by the following equation: $ID_{sc}(d)/ID_{tip}(d)=R$, where d is the needle penetration distance, $ID_{sc}(d)$ is the internal diameter of the most distal aspect of the snare (as indicated by the legend C in FIG. 3c) as a variable dependent on the penetration of the needle 10 into a tissue, and $ID_{tip}(d)$ is the internal diameter of the tip 40 which also may be dependent on forces that develop relative to the penetration of the needle a certain distance (d) into a tissue. In accordance with the present invention, the present applicant has discovered that R should be greater than or equal to one since as R increased, the potential interaction between the core specimen and the internal diameter (C) of the snare 16/inner tube 14 decreases. The internal diameters are described as variables dependent on the needle penetration distance (d), since it is possible, depending upon the structural integrity of the wall components, that external forces applied as the needle penetrates tissue could influence the specified internal diameters. The relationship between the internal diameter (C) of the snare and the internal diameter (B) of the distal tip 40 is shown in FIG. 3C.

In accordance with the present invention, there is a direct correlation between needle performance and the R averages and the ratio R provides a valid descriptor of intraluminal specimen transit and needle performance. According to a first embodiment R≧1.00; according to a second embodiment, R≧1.15; according to a third embodiment, R≧1.20; according to a fourth embodiment, R≧1.25; according to a fifth embodiment, R≧1.30; and according to a sixth embodiment, R≧1.35. It will be appreciated that the above values are merely exemplary in nature and that other values are equally suitable so long as the ratio R eliminates the occurrence of the obstruction phenomena that makes it difficult for the specimen to move forward into the needle 10 or compromises specimen recovery at the conclusion of the procedure.

It will also be appreciated that since R represents a ratio, small differences in the values of the numerator and denominator can result in substantial practical and physical implications influencing specimen transit and needle performance. The applicant has therefore discovered that an R average value of about 1.0 or less will produce a virtual obstruction, which is not desirable during the specimen capture and withdrawal procedure. This is in direct contrast to Applicant's previous patent where diameter equivalence between the distal tip 40 and the inner tube 14 was suggested and still consistent with the concept of avoiding a ridge or lip between the distal tip 40 and the inner tube 14 which could impede tissue entering the instrument.

The inner tube 14 is inserted until the snare 16 reaches the shoulder 42 provided on the interior of the outer cannula 12 at the position where the diameter changes as shown in FIG. 3C. However, other embodiments not requiring a shoulder are possible in which the outer surface of the inner tube is opposed to the inner surface of the outer tube, the two surfaces are bonded and the distal portion of the inner and outer tube are formed into a distal cutting tip.

With the gear or connector 30 extending proximal of the outer cannula's anchor 44, the cannula and snare assembly are attached to the handle piece 28 at the distal facing side 52 of the handle 22. The gear 30 of the inner tube 14 is inserted into a complementary hole 48 in the lever while the anchor 44 of the outer cannula 12 mates with a complementary hole 49 in the handle piece 28. Thus, when the lever 24 is rotated within its groove 26 with respect to the handle piece 28, the inner tube 14 will rotate with respect to the outer cannula 12. A cannula cap 50 is assembled onto the distal tip 40 of the cannula and threadedly engaged to the distal facing end 52 of the handle piece 28. In other embodiments, a non-threaded cannula cap or similar retaining member can be bonded to the distal facing end 52 of the handle piece 28 to ensure that the outer cannula 12 does not rotate or move longitudinally relative to the handle 28. The stylet 20 is inserted into the proximal end 32 of the inner tube until a distal tip portion 54 of the stylet extends beyond the distal tip 40 of the cannula. A stylet cap 56 can then be threadedly engaged to the proximal facing side 46 of the handle piece, covering the proximal end 58 of the stylet to prevent it from moving proximally within the inner tube 14. Other embodiments not requiring a stylet cap in which the proximal end of the stylet reversibly connects to the handle to prevent it from moving proximally are possible.

As can be seen in FIGS. 3a and 4, both the distal ends 40, 54 of the stylet and the outer cannula preferably have sloped end faces 60, 62 although it is not necessary. This improves the cutting actions of the both the stylet and the outer cannula by providing sharp leading edges 64. In this position, the stop 66 (FIG. 2) at the proximal end 58 (FIG. 1) of the stylet preferably mates with a complementary indent 68 (FIG. 7) in the handle piece 28 to maintain the rotational orientation of the stylet 20 with respect to the outer cannula 12 such that the slopes of the two distal ends 40, 54 are approximately parallel, or aligned optimally to result in an efficient piercing and cutting action and the stylet does not rotate relative to the outer cannula during the initial bone penetration. This is the configuration that would be used for initiating insertion of the biopsy needle 10 into the bony cortex.

As can be seen in FIG. 3b, which is a partial cutaway view, the free end 70 of the coil snare 16 includes a tab 72 that engages or is attached to a hole 74 (FIG. 4) on the interior surface of the outer cannula 12. This hole 74 preferably extends through the entire wall of the outer cannula. If desired, the tab 72 can be adhered to the hole 74 in the outer cannula through the use of adhesives, welding, or any known attachment process. However, it will be appreciated that the tab 72 and hole 74 can be eliminated and the outer surface of the inner tube can be bonded to the inner surface of the outer tube by welding or some other type of attachment method. It will therefore be appreciated that so long as the two structures are attached to one another, any number of different techniques can be used to accomplish such a coupling action, including the illustrated manner or using a direct bond between two surfaces, etc.

After the needle 10 is inserted into the marrow, the stylet 20 is removed proximally without any movement of the outer cannula 12 with respect to the patient, minimizing discomfort. As can be seen in FIG. 3c, marrow tissue may now enter the passageway within the outer cannula 12 through the distal end 40 of the outer cannula as the needle is advanced further and can enter the inner passageway of the inner tube 14, preferably to a position proximal of the snare 16.

Specimen transit refers to the process of specimen movement from the distal tip of the needle into the snare and inner tube lumen. The efficacy of specimen transit is modulated by the configuration of the tip and the relationship of ($ID_{sc}$) to ($ID_{tip}$). The advantages of snare capturing mechanisms are realized only by ensuring that specimen transit is maximized, according to the R value relationship.

Figure 3E:
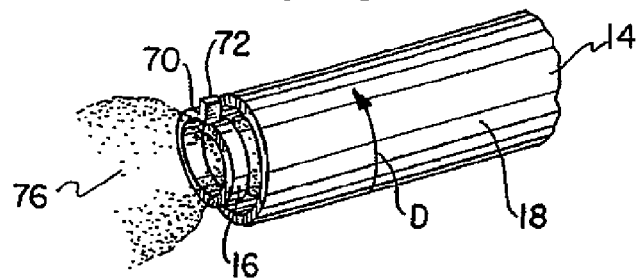
Figure 5:
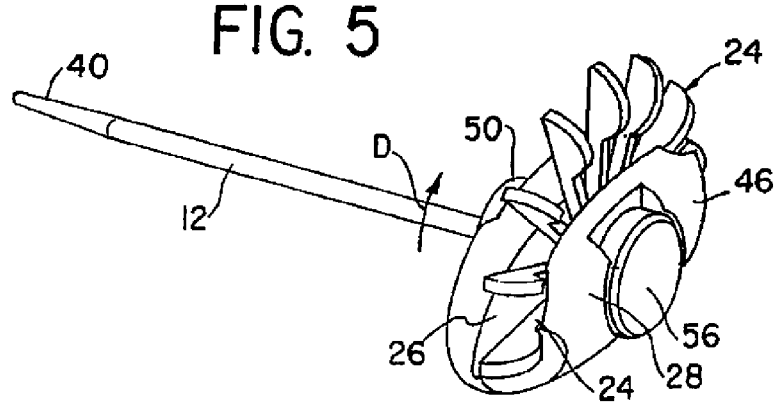
FIG. 5 is a perspective view of the biopsy needle showing operation by a physician.

To operate the snare 16, i.e. to cause cutting and/or holding of the biopsy piece 76 within the inner tube 14, the lever 24 attached to the proximal end 32 of the inner tube is rotated in the direction of arrow D as seen in FIGS. 3d-3e and 5. Of course, the snare 16 can be designed such that rotation in the opposite direction causes the same effect. With full rotation (180 degrees) of the lever 24, the inner tube 14 and snare 16 achieve a position similar to that shown in FIG. 3e, in which the inner tube 14 has been rotated approximately 180 degrees. Since the free end 70 of the snare is fixed to the outer cannula 12, the result of the rotation is that the coil of the snare 16 will tighten so that the cross-sectional area through the snare 16 is approximately less than a third of the area when in the open configuration.

It is also contemplated that any decrease, even a slight decrease, in the cross-sectional area of the snare will cause pressure on the biopsy piece 76. Therefore, while the current amount of rotation is preferred, it is not necessary for the proper functioning of the present invention.

As seen in FIG. 5, movement of the lever 24 can be independent of any movement of the handle piece 28 or the outer cannula 12. Therefore, the outer cannula 12, which is in direct contact with the patient while the sample is taken, can remain substantially stationary. As motion of the outer cannula 12 relative to the patient, a painful maneuver, is not required to sever and capture the specimen, incorporation of the snare mechanism limits painful needle manipulations.

With the tightening of the snare 16, there is a high probability that the biopsy piece 76 will remain in the needle 10 and will be recovered as the needle is removed so long as efficient specimen transit has facilitated the passage of the specimen into the lumen of the snare and the inner tube. If the tightening of the snare 16 does not immediately cause the biopsy piece 76 to be cut, it will be significantly squeezed and/or notched, such that rearward motion of the needle 10, which causes rearward pressure on any biopsy piece 76 proximal of the snare 16, will cause material proximal of the snare 16 to detach from material that is distal of the snare.

As can be seen in FIG. 7, the handle 22 includes several features designed for ease of use of the physician and ease of manufacture and construction. The handle piece 28 includes a groove 26 that holds the lever 24. The groove 26 has two notches 78 that generally protect the lever 24 from any accidental contact with the physician when in either the full-open or full-closed positions, but allow access to the lever. Further, the holes in the handle piece 28 that receive the anchor 44 of the outer cannula and the stop 66 of the stylet have complementary shapes in order to prevent rotation of those two components with respect to the handle, as previously discussed. The proximal and distal facing sides 46, 52 of the handle piece are also provided with threaded regions for receiving the cannula and stylet caps 50, 56.

Once the biopsy needle 10 has captured a cored specimen, it must be recovered for pathologic interpretation. The lever is rotated opposite to the direction D, thereby opening up the coil to its original diameter. An obturator is placed through the tip of the needle and the specimen is pushed through the inner tube and through the handle for collection. As initial efficient specimen transit into the inner tube influences transit of the specimen through the remainder of the inner cannula during the specimen recovery phase of the procedure, maximizing the R value also positively influences specimen recovery. Once the specimen has been ejected and recovered, the biopsy needle 10 is then ready to be sterilized for its next use. If necessary, the entire biopsy needle can be disassembled, although the tab 72 at the free end of the snare must be disengaged from the hole 74 in the outer cannula. This can be accomplished with any small tool pushed through hole 74. If the free end 70 of the snare is permanently adhered to the outer cannula 12, it then may be necessary to sterilize the outer cannula and inner tube as a single unit. However, due to the few number of parts and relative ease and low cost of construction of the present needle, it is also contemplated that such a device is easily disposable.

FIG. 6b shows another embodiment where the snare 16 is not located at the distalmost section of the inner tube 14 but instead is spaced slightly inward from the distal end. A distal end section 91 is provided and in this embodiment (as mentioned above), the inner tube 14 is not attached to the outer cannula via a tab and opening but instead, the inner tube 14 can be attached by means of the distal end section 91. It will be appreciated that the most distal inner diameter of the inner tube 14 at the most distal aspect of section 91, designated as $ID_{int}$, defines the ratio $R=(ID_{int})/(ID_{tip})$ When the most distal portion of the inner tube 14 is the most distal portion of the snare 16, the ratio is defined as $(ID_{sc})/(ID_{tip})$ since $ID_{sc}=ID_{int}$; however, when a small portion (section 91) of the inner tube 14 is distally located relative to the snare 16, the ratio R is $=(ID_{int})/(ID_{tip})$, where $(ID_{int})$ is the inner diameter of the most distal portion of the inner tube 14. It will be appreciated that the distal end section 91 can have a diameter that is different than the diameter of the adjacent snare 16.

Thus, it can be seen that a low cost, simply-manufactured biopsy needle will attain improved results over known devices, not only in the success rate of the marrow extraction procedures, but also a marked increase in patient comfort throughout the procedure. High performance needles require not only efficient specimen capture but efficient specimen transit through the needle. One desirable side benefit of this increased comfort might be increased participation in bone marrow donor programs for transplant candidates.

While the embodiments shown and described above are fully capable of achieving the objects and advantages of the present invention, it is to be understood that these embodiments are shown and described solely for the purposes of illustration and not for limitation.

What is claimed is:

1. A biopsy needle for removal of tissue from a patient comprising:
    an outer tube having a distal end that has an inner diameter $(ID_{tip})$;
    an inner tube within said outer tube; and
    a snare having a first proximal end connected to the inner tube and a second distal end connected to the outer tube and having an inner distal diameter $(ID_{sc})$, wherein said snare is contained within the outer tube such that the distal end of the outer tube is located distal to the second distal end of the snare and the snare has a variable diameter that is controlled by rotation of the inner tube with respect to the outer tube in a prescribed direction resulting in the opening and closing, respectively, of the snare, wherein a ratio $(R)=(ID_{sc})/(ID_{tip})$ is greater than 1.

2. The biopsy needle of claim 1, wherein R is greater than 1.15.

3. The biopsy needle of claim 1, wherein R is greater than 1.20.

4. The biopsy needle of claim 1, wherein R is greater than 1.25.

5. The biopsy needle of claim 1, wherein R is greater than 1.30.

6. The biopsy needle of claim 1, wherein R is greater than 1.35.

7. The biopsy needle of claim 1, wherein the outer tube has a first section with a first diameter and a second section located at a distalmost portion that has a second diameter that is less than the first diameter, the second diameter defining the inner diameter $(ID_{tip})$.

8. The biopsy needle of claim 1, wherein the snare has a first position and a second position, wherein in the first position, the snare has a first diameter and in the second position, the snare has a second diameter that is less than the first diameter, the snare being moved from the first position to the second position by rotation of the inner tube with respect to the outer tube in one direction and being moved from the second position to the first position by rotation in an opposite direction.

9. The biopsy needle of claim 1, wherein the snare is integral with the inner tube.

10. The biopsy needle of claim 1, wherein the snare comprises a helical coil.

11. A reusable biopsy needle comprising:
an outer tube having a distal end that has an inner diameter ($ID_{tip}$); and
an inner tube within said outer tube and having an inner diameter ($ID_{int}$) at its most distal aspect which is located proximal to the distal end of the outer tube, the inner tube having means for holding a biopsy sample with a force sufficient to detach a biopsy sample from the surrounding tissue when the biopsy needle is withdrawn, the means being entirely located within the outer tube and having one portion connected to the inner tube and another portion connected to the outer tube, the means being elastically deformable so that the biopsy needle can be reused without withdrawing the biopsy needle, wherein a ratio $(R)=(ID_{int})/(ID_{tip})$ is greater than 1.

12. The biopsy needle of claim 11, wherein R is greater than 1.15.

13. The biopsy needle of claim 11, wherein R is greater than 1.20.

14. The biopsy needle of claim 11, wherein R is greater than 1.25.

15. The biopsy needle of claim 11, wherein R is greater than 1.30.

16. The biopsy needle of claim 11, wherein R is greater than 1.35.

17. A biopsy needle for removal of tissue from a patient comprising:
an outer tube having a distal end that has an inner diameter ($ID_{tip}$);
an inner tube within said outer tube; and
a snare formed as part of the inner tube near a distal end of the inner tube but offset and spaced from the distal end of the inner tube so as to define a distal end section of the inner tube between the snare and the distal end, the distal end section being connected to the outer tube so as to locate the snare entirely within the outer tube and wherein the distal end section has an inner distal diameter ($ID_{int}$), wherein said snare has a variable diameter that is controlled by rotation of the inner tube with respect to the outer tube in a prescribed direction resulting in the opening and closing, respectively, of the snare, wherein a ratio $(R)=(ID_{int})/(ID_{tip})$ is greater than 1.

18. A biopsy needle for removal of tissue from a patient comprising:
an outer tube having a distal end that has an inner diameter ($ID_{tip}$);
an inner tube within said outer tube; and
a snare that is an integral part of the inner tube and having a distal end connected to the outer tube, the snare having an inner distal diameter ($ID_{sc}$), wherein said snare has a variable diameter that is controlled by rotation of the inner tube with respect to the outer tube in a prescribed direction resulting in the opening and closing, respectively, of the snare, wherein the distal end of the outer tube that is defined by the inner diameter ($ID_{tip}$) is located more distally than the snare and; wherein a ratio $(R)=(ID_{sc})/(ID_{tip})$ is greater than 1.

* * * * *